(12) United States Patent
Chen et al.

(10) Patent No.: US 10,512,445 B2
(45) Date of Patent: Dec. 24, 2019

(54) MULTI-MODE ULTRASOUND DEVICE AND METHOD FOR ASSESSING A BONE OF A SUBJECT WITH COUPLER SENSING CONFIGURATIONS OF PROBES

(71) Applicant: KONINKLIJKE PHILIPS N.V., Eindhoven (NL)

(72) Inventors: Jiangang Chen, Shanghai (CN); Jingping Xu, Shanghai (CN)

(73) Assignee: Koninklijke Philips N.V., Eindhoven (NL)

( * ) Notice: Subject to any disclaimer, the term of this patent is extended or adjusted under 35 U.S.C. 154(b) by 241 days.

(21) Appl. No.: 15/110,969

(22) PCT Filed: Jan. 14, 2015

(86) PCT No.: PCT/EP2015/050525
§ 371 (c)(1),
(2) Date: Jul. 12, 2016

(87) PCT Pub. No.: WO2015/113813
PCT Pub. Date: Aug. 6, 2015

(65) Prior Publication Data
US 2016/0338663 A1 Nov. 24, 2016

(30) Foreign Application Priority Data

Jan. 17, 2014 (WO) ................ PCT/CN2014/070764
Apr. 30, 2014 (EP) ...................................... 14166494

(51) Int. Cl.
*G01N 29/00* (2006.01)
*A61B 8/15* (2006.01)
(Continued)

(52) U.S. Cl.
CPC .............. *A61B 8/0875* (2013.01); *A61B 8/14* (2013.01); *A61B 8/4218* (2013.01);
(Continued)

(58) Field of Classification Search
CPC ....... A61B 8/0875; A61B 8/14; A61B 8/4218; A61B 8/4477; A61B 8/4245;
(Continued)

(56) References Cited

U.S. PATENT DOCUMENTS

| 4,941,474 A | * | 7/1990 | Pratt, Jr. | .............. | A61B 8/0875 600/437 |
| 5,458,130 A | | 10/1995 | Kaufman et al. | | |

(Continued)

FOREIGN PATENT DOCUMENTS

| CN | 1040739 A | 3/1990 |
| CN | 1528242 A | 9/2004 |

(Continued)

*Primary Examiner* — Amanda Lauritzen Moher
*Assistant Examiner* — Chao Sheng

(57) ABSTRACT

An embodiment of this invention provides an ultrasound device that assesses a bone of a subject in at least two modes comprising a first mode and a second mode. The ultrasound device comprises: a selecting unit configured to select a mode from the at least two modes; a first ultrasound probe configured to transmit an ultrasound signal to the bone; a second ultrasound probe configured to receive the ultrasound signal from the bone; an assessing unit configured to derive a first parameter of the bone based on the selected mode and the ultrasound signal received by the second ultrasound probe; and a coupler being configured to be switched to a first configuration in the first mode and to a second configuration in the second mode. The ultrasound probes are oriented in substantially a same direction in the first configuration, and in substantially an opposite direction in the second configuration.

21 Claims, 6 Drawing Sheets

(51) Int. Cl.
*A61B 8/14* (2006.01)
*A61B 8/08* (2006.01)
*A61B 8/00* (2006.01)
*A61B 6/00* (2006.01)

(52) U.S. Cl.
CPC .......... *A61B 8/4245* (2013.01); *A61B 8/4254* (2013.01); *A61B 8/4444* (2013.01); *A61B 8/4477* (2013.01); *A61B 6/505* (2013.01); *A61B 8/15* (2013.01); *A61B 8/429* (2013.01); *A61B 8/4263* (2013.01); *G01N 29/00* (2013.01); *G01N 2291/02483* (2013.01)

(58) Field of Classification Search
CPC ... A61B 8/4254; A61B 8/4263; A61B 8/4444; A61B 8/15; A61B 8/419; G01N 2291/02483; G01N 29/00
See application file for complete search history.

(56) References Cited

U.S. PATENT DOCUMENTS

| | | | |
|---|---|---|---|
| 6,468,215 | B1 | 10/2002 | Sarvazyan et al. |
| 6,899,680 | B2 * | 5/2005 | Hoff ..................... A61B 8/0875 600/449 |
| 7,537,566 | B2 | 5/2009 | Mano et al. |
| 7,833,161 | B2 | 11/2010 | Ghosh et al. |
| 2002/0161300 | A1 | 10/2002 | Hoff et al. |
| 2005/0004457 | A1 * | 1/2005 | Moilanen ............. A61B 8/0875 600/437 |
| 2005/0197576 | A1 | 9/2005 | Luo et al. |
| 2007/0232916 | A1 * | 10/2007 | Waki .................... A61B 5/6843 600/444 |
| 2009/0018445 | A1 | 1/2009 | Schers et al. |
| 2010/0262013 | A1 * | 10/2010 | Smith ...................... A61B 8/00 600/459 |
| 2011/0040187 | A1 * | 2/2011 | Matsumura .......... A61B 5/6843 600/443 |
| 2012/0095347 | A1 * | 4/2012 | Adam ...................... A61B 8/12 600/459 |
| 2012/0253196 | A1 | 10/2012 | Nagata et al. |
| 2013/0338503 | A1 * | 12/2013 | Cohen ................. A61B 8/4411 600/443 |
| 2014/0114194 | A1 | 4/2014 | Kanayama et al. |
| 2015/0126864 | A1 * | 5/2015 | Buelow ................ A61B 8/0825 600/437 |

FOREIGN PATENT DOCUMENTS

| | | |
|---|---|---|
| CN | 102293668 A | 12/2011 |
| JP | 2003275209 A | 9/2003 |
| WO | 8002796 A1 | 12/1980 |
| WO | 9001903 A1 | 3/1990 |
| WO | 2005122905 A1 | 12/2005 |
| WO | 2011119873 A2 | 9/2011 |
| WO | 2013005776 A1 | 1/2013 |

* cited by examiner

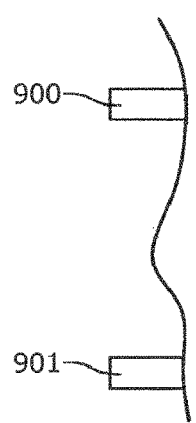
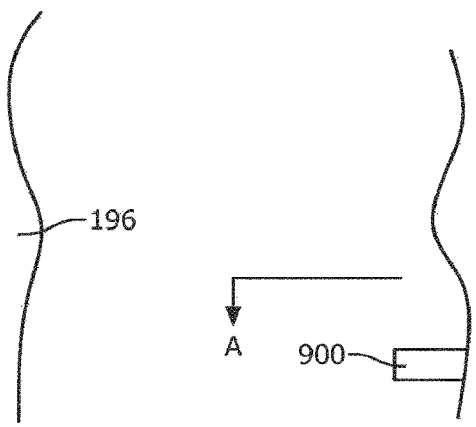
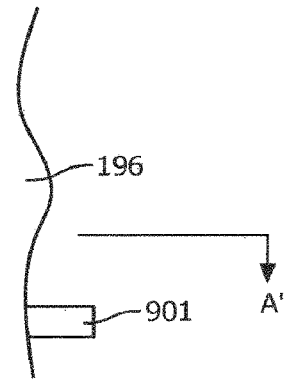
FIG. 1a (Prior Art)         FIG. 1b (Prior Art)
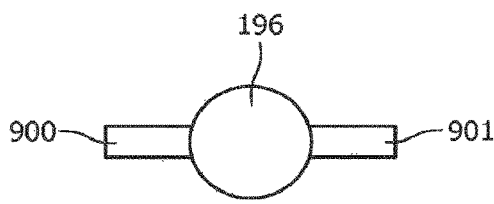
FIG. 1c (Prior Art)
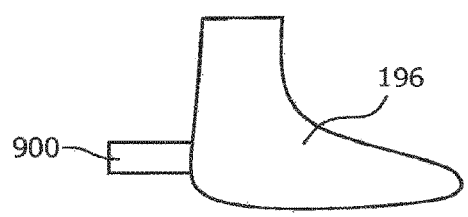
FIG. 1d (Prior Art)

MULTI-MODE ULTRASOUND DEVICE AND METHOD FOR ASSESSING A BONE OF A SUBJECT WITH COUPLER SENSING CONFIGURATIONS OF PROBES

This application is the U.S. National Phase application under 35 U.S.C. § 371 of International Application No. PCT/EP2015/050525, filed on Jan. 14, 2015, which claims the benefit of European Patent Application No. 14166494.6, filed Apr. 30, 2014, and of International Application No. PCT/CN2014/070764, filed Jan. 17, 2014. These applications are hereby incorporated by reference herein.

FIELD OF THE INVENTION

This invention mainly relates to the field of ultrasound, more particularly, to an ultrasound device and a method of assessing a bone of a subject.

BACKGROUND OF THE INVENTION

Osteoporosis increases the risk of fracture and has become a significant public health threat nowadays in the world. It is very important to diagnose osteoporosis in a very early stage. Quantitative Ultrasound (QUS) has become a widely available non-invasive tool for assessment of bone status and diagnosis of osteoporosis.

There are mainly three approaches for QUS measurement in the prior art.

The first approach is based on the axial transmission mode (cf. U.S. Pat. No. 7,112,173 B1, U.S. Pat. No. 7,022,076 B1, U.S. Pat. No. 6,221,019 B1). Representative commercial devices include Omnisense 7000 and Omnisense 8000 (BeamMed Ltd, Israel). As shown in FIG. 1a, a pair of probes 900, 901 are placed in tandem on one side of the bone 196. The axial transmission mode is suitable for assessing long bones such as tibia and radius. Here a tibia ultrasound assessment device is used as an example. The pair of probes 900, 901 are fixed on a bracket (not shown) which is connected to a pedal (not shown) on which a subject can stand. When the subject stands on the pedal, the pair of probes 900, 901 are in tandem on one side of the tibia.

The second approach is based on the transverse transmission mode. Representative commercial devices include Express (GE®, US), SONOST-3000 (Osteosys®, Korea), Osteo Pro (BMTECH®, Korea). As shown in FIG. 1b, which is a side view of a bone, and FIG. 1c, which is a corresponding profile taken on the line AA' in FIG. 1b, a pair of probes 900, 901 are placed in opposite direction across the bone 196. The transverse transmission mode is suitable for status evaluation of cancellous bones such as the heel pad (cf. Patent No. US2003/0068014 A1, U.S. Pat. No. 6,676, 291 B2), bone thickness measurement (cf. U.S. Pat. No. 7,537,566 B2) and age evaluation (cf. U.S. Pat. No. 7,678, 049B2). The bracket and pedal structure may be similar to that used for the axial transmission mode.

The third approach is based on the pulse-echo mode. Related technologies include ultrasound critical-angle reflectometry (UCR) (cf. Patent No. US20050015010; U.S. Pat. No. 6,899,680) and backscattering techniques (cf. Patent No. US20020161300). The pulse-echo mode takes advantage of wave reflection or scattering at the soft tissue-bone and cortical-trabecular bone interface, and is able to assess bone material properties and microstructures. As seen in FIG. 1d, a probe 900 transmits an ultrasound signal to the bone 196 and receives an echo signal of the ultrasound signal from the bone 196. The bracket and pedal structure may be similar to that used for the axial transmission mode.

WO 2011/119873 A2 discloses ultrasound guided automated wireless distraction osteogenesis, wherein the ultrasound transceivers are mounted to the bone, subcutaneously on two sides of the osteotomy.

SUMMARY OF THE INVENTION

The inventors of the present application have realized that the existing three approaches for QUS measurement have the following drawbacks.

Limited skeletal sites. Transverse mode and pulse-echo mode are only applicable to one skeletal site, e.g. heel pad. Axial transmission mode is only applicable to long bones. As a result, the evaluation of bone health status is unilateral.

Limited parameters. Each of axial transmission mode, transverse mode and pulse-echo mode only provides limited parameters, which can only reflect a few aspects of bone material properties.

Limited measurement points. Most approaches take the measurement at a single point at a specific skeletal site (e.g., heel pad), resulting in poor accuracy and reliability.

Single mode. The existing approaches are based on one of axial transmission mode, transverse transmission mode and QUS pulse-echo mode. In the case of, for example, the tibia ultrasound assessment device, the location relationship of the bracket and the pedal are fixed specifically for assessing the tibia, therefore it cannot be used in e.g. the transverse transmission mode to assess a cancellous bone. No ultrasound assessment device in the prior art can support both the axial transmission mode and the transverse mode. The ultrasound assessment device in the prior art lacks flexibility of use.

Poor repeatability. Most approaches take the measurement at only selected points, resulting in poor repeatability.

Operator-dependent. Most devices must be manipulated by experienced doctors. The experience of the operator may influence the accuracy of the evaluation.

Ignorance of the coupling effect of soft tissue. Soft tissue was reported to have a significant coupling effect on the ultrasound propagation in bones, including varying the propagation velocity in bones. Such an effect may introduce bias to the evaluation if it is not considered in in vivo measurement. In the existing approaches, such a coupling effect of the soft tissue is not considered, and only the thickness of the soft tissue is considered to derive how long the ultrasound signal propagates in the soft tissue.

Based on the prior art described above, it is advantageous to provide an improved ultrasound bone assessment device, which overcomes at least one of the above-described drawbacks.

According to an embodiment of this invention, it proposes an ultrasound device for assessing a bone of a subject in at least two modes comprising a first mode and a second mode. The ultrasound device comprises: a selecting unit configured to select a mode from the at least two modes; a first ultrasound probe having a first face to be brought into contact with skin of the subject and configured to transmit an ultrasound signal to the bone; a second ultrasound probe having a second face to be brought into contact with skin of the subject and configured to receive the ultrasound signal from the bone; an assessing unit configured to derive a first parameter indicating one or more characteristics of the bone based on the selected mode and the ultrasound signal received by the second ultrasound probe in the first mode or in the second mode; and a coupler for coupling the first ultrasound probe and the second ultrasound probe, the coupler being configured to be switched to a first configuration in the first mode and to a second configuration in the second mode, wherein the first face and the second face are oriented in substantially a same direction in the first configuration, and in substantially an opposite direction in the second configuration.

As is well known, the face of an ultrasound probe is defined as a surface of the ultrasound probe which is to contact skin of the subject during bone assessment. The face of the ultrasound probe can be flat or curved. During the operation of the ultrasound probe, the ultrasound signal propagates in a "range" direction which is defined as a direction orthogonal to the face of the ultrasound probe.

In the first mode, since the face of the first ultrasound probe (i.e. the first face) and the face of the second ultrasound probe (i.e. the second face) are oriented in substantially a same direction, the ultrasound device is applicable for bone assessment in the axial transmission mode. In the second mode, since the face of the first ultrasound probe and the face of the second ultrasound probe are oriented in substantially an opposite direction, the ultrasound device is applicable for bone assessment in transverse mode.

Since the ultrasound device is switchable between a first mode and a second mode, it can support both the axial transmission mode and the transverse mode, resulting in a high flexibility of use for the ultrasound assessment device.

According to an embodiment, the ultrasound signal comprises a first ultrasound sub-signal in a first frequency band and/or a second ultrasound sub-signal in a second frequency band, and the second frequency band is higher than the first frequency band.

In this way, the ultrasound device is capable of transmitting the ultrasound signal in more than one frequency band, which further increases its flexibility of use, because a certain assessment may be performed better with an ultrasound signal in a low frequency band, whilst a certain other assessment may be performed better with an ultrasound signal in a high frequency band. For example, an ultrasound signal with a central frequency in a range from 0.5 MHz to 1 MHz is suitable for assessing bone properties, whilst an ultrasound signal with a central frequency around 5 MHz is suitable for acquiring M-mode ultrasound imaging, which can be used to determine soft tissue thickness for example. Consequently, it has the advantage of providing the possibility of taking the impact of the layer of soft tissue around the bone on bone assessment into account so as to improve the accuracy of the bone assessment.

According to an embodiment, the assessing unit is configured to derive a third parameter based on the second ultrasound sub-signal, the third parameter indicating a coupling effect caused by soft tissue around the bone, and to derive the first parameter based on the first ultrasound sub-signal and the derived third parameter, the first parameter indicating one or more characteristics of the bone.

In this way, the accuracy of bone assessment can be improved, because the coupling effect of the layer of soft tissue overlying the bone has been considered in assessing the bone.

According to an embodiment, at least one ultrasound probe of the first ultrasound probe and the second ultrasound probe further comprises at least one pressure sensor for measuring pressure applied to the face of the at least one ultrasound probe; and the assessing unit is configured to derive the first parameter based on the received ultrasound signal and the measured pressure.

Because the pressure at the probe-skin interface influences the thickness of the soft tissue and thus has an important influence on the assessment result, it is beneficial to have at least one pressure sensor for measuring the pressure applied to the face of the probe, and only if e.g. the measured pressure is within the reasonable range, the assessment result is adopted. In this manner, the accuracy of the assessment result can be improved.

According to an embodiment, the one or more pressure sensors are three pressure sensors, the distance between any two of the three pressure sensors being constant.

Such a way of adopting three pressure sensors arranged at a constant mutual distance provides the benefit that the face of the probe is kept in proper contact with the skin of the subject being subjected to a measurement. For example, if the three pressures measured by the three pressure sensors all fall in a predetermined range, this indicates a good positioning of the probe on the skin of the subject, i.e. the face of the probe properly contacts the skin of the subject.

According to an embodiment, each of the ultrasound transducers contained in the first ultrasound probe and/or the second ultrasound probe is movable over a certain range so as to measure at a plurality of sites on the subject, the assessing unit is configured to derive the first parameter at each of the plurality of sites, and the ultrasound device further comprises an averaging unit configured to average the first parameters derived at the plurality of sites to obtain an averaged first parameter.

Because each of the ultrasound transducers is movable over a certain range so as to measure at a plurality of sites on the subject, the assessing unit can derive the first parameter at each of the plurality of sites for averaging by the averaging unit. Then the averaged assessment result can be more accurate than the assessment result that is based only on a single site.

According to an embodiment of this invention, it proposes a method of assessing a bone of a subject in at least two modes comprising a first mode and a second mode, using an ultrasound device mentioned above, said method comprising: selecting a mode of the at least two modes; transmitting an ultrasound signal to the bone using a first ultrasound probe; receiving the ultrasound signal from the bone using a second ultrasound probe; and deriving a first parameter indicating one or more characteristics of the bone based on the selected mode and the ultrasound signal received by the second ultrasound probe in the first or second mode.

DESCRIPTION OF THE DRAWINGS

The present invention will be described and explained hereinafter in more detail in combination with embodiments and with reference to the drawings, wherein:

FIG. 1a illustrates the usage status of a pair of probes in an approach based on the axial transmission mode in the prior art;

FIG. 1b illustrates the usage status of a pair of probes in an approach based on the transverse transmission mode in the prior art;

FIG. 1c is a profile shown in the direction AA' in FIG. 1b;

FIG. 1d illustrates the usage status of a probe in an approach based on the pulse-echo mode in the prior art;

Figure 2:
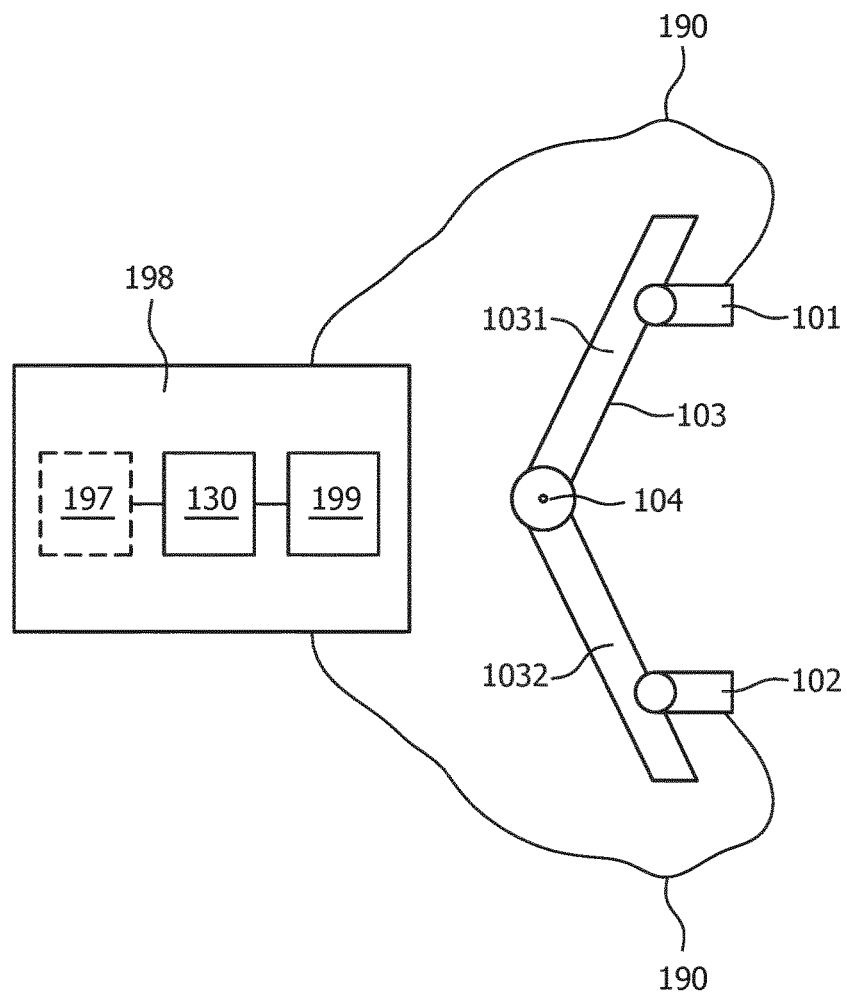
FIG. 2 illustrates an ultrasound device for assessing a bone of a subject according to an embodiment of this invention.

The same reference signs in the figures indicate similar or corresponding features and/or functionalities.

DETAILED DESCRIPTION

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn to scale for illustrative purposes.

FIG. 2 illustrates an ultrasound device 1 for assessing a bone of a subject in at least two modes comprising a first mode and a second mode according to an embodiment of this invention. The ultrasound device 1 comprises a selecting unit 199, a first ultrasound probe 101, a second ultrasound probe 102, an assessing unit 130, and a coupler 103. The selecting unit 199 is configured to select a mode from the at least two modes. The first ultrasound probe 101 is configured to transmit an ultrasound signal to the bone. The second ultrasound probe 102 is configured to receive the ultrasound signal from the bone. The assessing unit 130 is configured to derive a first parameter indicating one or more characteristics of the bone based on the selected mode and the ultrasound signal received by the second ultrasound probe 102 in the first mode or in the second mode. The coupler 103 couples the first ultrasound probe 101 and the second ultrasound probe 102, the coupler 103 being configured to be switched to a first configuration in the first mode and to a second configuration in the second mode. A face 109 of the first ultrasound probe and a face 110 of the second ultrasound probe are oriented in substantially a same direction in the first configuration, and in substantially an opposite direction in the second configuration.

It is appreciated by those skilled in the art that, although in the above embodiment, the first ultrasound probe 101 is configured to transmit an ultrasound signal to the bone and the second ultrasound probe 102 is configured to receive the ultrasound signal from the bone, the second ultrasound probe 102 may be further configured to transmit an ultrasound signal to the bone and the first ultrasound probe 101 may be further configured to receive the ultrasound signal from the bone. In such a case, the assessing unit 130 is further configured to derive the first parameter based on the selected mode and the ultrasound signal received by the first ultrasound probe 101 in the first mode or in the second mode. In another embodiment, the first parameter may be derived twice. The first ultrasound probe 101 transmits an ultrasound signal to the bone and the second ultrasound probe 102 receives the ultrasound signal from the bone so as to derive the first parameter for the first time. The second ultrasound probe 102 transmits an ultrasound signal to the bone and the first ultrasound probe 101 receives the ultrasound signal from the bone so as to derive the first parameter for the second time. Then the first parameter derived for the first time and the first parameter derived for the second time are averaged to derive the final first parameter.

The ultrasound device 1 can be used to assess bone of human beings or animals. The ultrasound device 1 can be used either for homecare or initial evaluation in a hospital, or follow-up after surgeries, e.g., monitoring of bone fracture healing.

The ultrasound device 1 can operate in any of the at least two modes. In the first mode, since the face of the first ultrasound probe and the face of the second ultrasound probe are oriented in substantially a same direction, the ultrasound device is applicable for bone assessment in axial transmission mode. In the second mode, since the face of the first ultrasound probe and the face of the second ultrasound probe are oriented in substantially an opposite direction, the ultrasound device is applicable for bone assessment in transverse mode. The at least two modes may further include other modes. As will be described below, in a third mode, the ultrasound device is applicable for bone assessment in pulse-echo mode.

The selecting unit 199 can be realized in many ways. For example, as shown in FIG. 2, the selecting unit 199 and the assessing unit 130 are accommodated in a case 198. The selecting unit 199 may be a knob on the surface of the case. It selects a mode in response to the user's rotation of the knob. Or, the selecting unit 199 may be in the form of a number of buttons on the surface of the case. It selects a mode in response to the user's pressing of the buttons. The selecting unit 199 may be also a keyboard, a touchscreen, etc.

In response to a selected mode, the assessing unit 130 performs the corresponding assessment. For example, the assessing unit 130 stores algorithms for different modes. In response to the selected mode, the assessing unit 130 may select the corresponding algorithms to derive a corresponding first parameter based on the ultrasound signal received by the second ultrasound probe.

In the first mode, the first parameter is e.g. a geometric and mechanical property of a bone. In the second mode, the first parameter is e.g. SOS or BUA. There may be different algorithms for different first parameters, e.g. for speed of sound (SOS) or for broadband ultrasound attenuation (BUA), in the same mode. In an embodiment, the selecting unit 199 may be also used to select a first parameter in the same mode. When a specific first parameter is selected by the selecting unit 199, the corresponding algorithm for that specific first parameter is performed by the assessing unit 130.

According to an embodiment, the assessing unit 130 derives the first parameter based not only on the selected mode and the ultrasound signal received by the second ultrasound probe 102, but also based on a received fourth parameter indicating a distance between the first ultrasound probe 101 and the second ultrasound probe 102. In some examples, the first parameter can be derived only from the ultrasound signal received by the second ultrasound probe 102. In some other examples, the first parameter such as SOS is derived from the ultrasound signal received by the second ultrasound probe 102 and the distance between the first ultrasound probe 101 and a second ultrasound probe 102. In the case of deriving the first parameter, such as SOS, a fourth parameter indicating a distance between the first ultrasound probe 101 and the second ultrasound probe 102 is acquired as an input to the assessing unit 130. In an embodiment, the fourth parameter can be input to the assessing unit 130 by means of a user input to the ultrasound device. In another embodiment, it is derived according to the following explanation with reference to FIGS. 3a-b, 4a-b.

The first ultrasound probe 101 and the second ultrasound probe 102 are e.g. connected to the case 198 via wired or wireless communication links 190. In an embodiment, the selecting unit 199 may be also a knob (not shown) intercommunicating with the case 198 via on communication links 190.

According to an embodiment, the at least two modes comprise a third mode. When the ultrasound device operates in the third mode, it is applicable for bone assessment in pulse-echo mode. In the third mode, the first ultrasound probe 101 is further configured to transmit an ultrasound signal to the bone and receive an echo signal of the ultrasound signal from the bone. The assessing unit 130 is further configured to derive a second parameter indicating one or more other characteristics of the bone based on the selected mode and the echo signal received by the first ultrasound probe 101 in the third mode., The second ultrasound probe 101 may not operate in this mode.

Additionally or alternatively, the second ultrasound probe 102 can be used to perform bone assessment in pulse-echo mode as well. In this case, the second ultrasound probe 102 is further configured to transmit an ultrasound signal to the bone and receive an ultrasound echo from the bone, and the assessing unit 130 is further configured to derive a second parameter indicating one or more other characteristics of the bone based on the selected mode and the echo signal received by the second ultrasound probe 102.

The second parameter is e.g. a bone material property. When the third mode is selected by the selection unit 199, the corresponding algorithm in the assessing unit 130 is performed.

The first ultrasound probe 101, the second ultrasound probe 102 and the coupler 103 can be realized in many ways. Some ways are discussed in detail in the following.

In an embodiment, the coupler 103 comprises two arms 1031, 1032 which have an adjustable intersection angle. In an example, the two arms is configued to be pivotable around an axis 104 so as to enable the intersection angle to be adjustable. Further, the first ultrasound probe 101 and the second ultrasound probe 102 are respectively rotatably coupled to ends of the two arms remote from the axis 104.

Figure 3A:
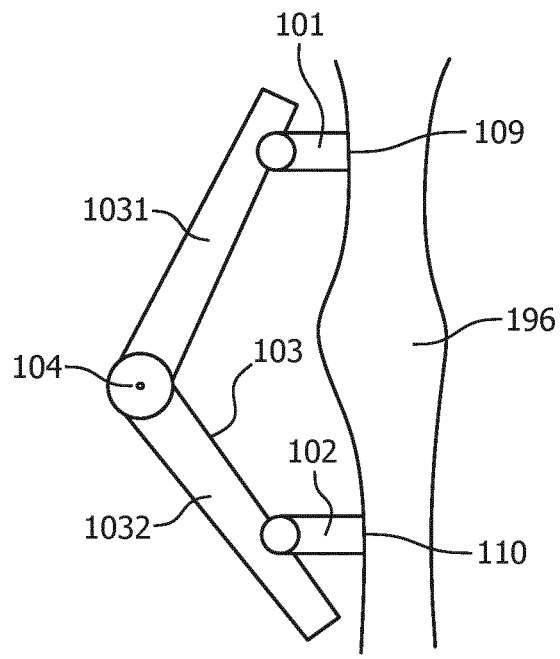
FIG. 3a illustrates a first configuration of the coupler when the coupler comprises two arms pivoting around an axis according to an embodiment of this invention.

FIG. 3a illustrates a first configuration of the coupler 103 in this embodiment. In the first mode (e.g. the axial transmission mode), the coupler 103 is in the first configuration, so that the intersection angle of the two arms is larger than that in the second configuration and thus suitable for assessing e.g. a long bone in the first mode.

Figure 3B:
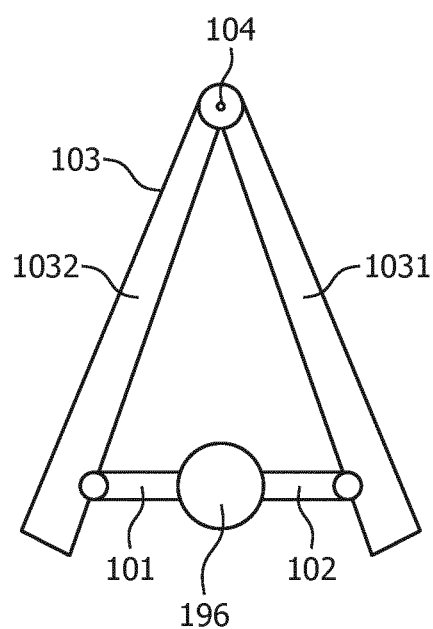
FIG. 3b illustrates a second configuration of the coupler when the coupler comprises two arms pivoting around an axis according to an embodiment of this invention.

FIG. 3b illustrates a second configuration of the coupler 103 in this embodiment. In the second mode (e.g. the transverse transmission mode), the coupler 103 is in the second configuration, so that the intersection angle of the two arms 1031, 1032 is smaller than that in the first configuration and thus suitable for assessing e.g. cancellous bones, such as a heel pad, in the second mode.

The first ultrasound probe 101 and the second ultrasound probe 102 are respectively rotatably coupled to ends of the two arms. For example, each of the first ultrasound probe 101 and the second ultrasound probe 102 is pivoted to the corresponding arm pivoting around an axis. By virtue of being rotatably coupled to ends of the two arms, each of the first ultrasound probe 101 and the second ultrasound probe 102 can—more—easily contact the skin of the subject.

In the embodiments in FIG. 3a and FIG. 3b, the fourth parameter indicating a distance between the first ultrasound probe 101 and the second ultrasound probe 102 can be determined from an intersection angle of the two arms, an angle between the "range" direction of the first ultrasound probe 101 and the arm which it is coupled to, and an angle between the "range" direction of the second ultrasound probe 102 and the arm which it is coupled to. The "range" direction of an ultrasound probe is to be taken to mean the direction orthogonal to the face of the ultrasound probe as introduced above. The intersection angle of the two arms, the angle between the "range" direction of the first ultrasound probe 101 and the arm which it is coupled to, and the angle between the "range" direction of the second ultrasound probe 102 and the arm which it is coupled to can be measured and then input to the assessing unit 130 manually. As an alternative, the intersection angle of the two arms, the angle between the "range" direction of the first ultrasound probe 101 and the arm which it is coupled to, and the angle between the "range" direction of the second ultrasound probe 102 and the arm which it is coupled to, can be obtained by measuring the orientation of the probes and the arms by means of gravity sensors e.g. disposed on the two arms, the first ultrasound probe 101 and the second ultrasound probe 102, and automatically input to the assessing unit 130. Then the assessing unit 130 can derive the fourth parameter based on these parameters.

In another embodiment, the fourth parameter indicating a distance between the first ultrasound probe 101 and the second ultrasound probe 102 can be measured by a laser measurement method. For example, a laser emitter is located within the first ultrasound probe 101 and a laser receiver is located within the second ultrasound probe 102. Based on laser speed and the propagation time from the laser emitter to the laser receiver, the fourth parameter indicating a distance between the first ultrasound probe 101 and the second ultrasound probe 102 can be calculated with high accuracy.

In another embodiment, the coupler 103 comprises two non-retractable portions 105, 106 and a retractable portion 107 arranged therebetween, which is retractable to different lengths, as required, into the two non-retractable portions 105, 106. An angle between any of the two non-retractable portions 105, 106 and the retractable portion 107 is adjustable. The first ultrasound probe 101 and the second ultrasound probe 102 are respectively rotatably coupled to the two non-retractable portions 105, 106 (e.g. by pivot axes, etc.).

By virtue thereof, each of the first ultrasound probe 101 and the second ultrasound probe 102 can—more—easily contact the skin of the subject by making the angle between any of the two non-retractable portions 105, 106 and the retractable portion 107 adjustable and by rotatably coupling the first ultrasound probe 101 and the second ultrasound probe 102 to the two non-retractable portions 105, 106.

Figure 4A:
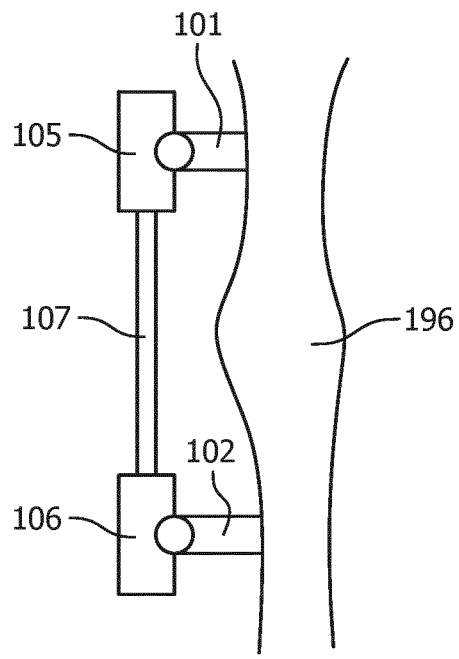
FIG. 4a illustrates a first configuration of the coupler when the coupler comprises a retractable portion which can be retracted into two non-retractable portions according to an embodiment of this invention.

FIG. 4a illustrates a first configuration of the coupler 103 in this embodiment. In the first mode (e.g. the axial transmission mode), the coupler 103 is in the first configuration, so that the retracted length of the retractable portion 107, an angle between the non-retractable portion 105 and the retractable portion 107, an angle between the non-retractable portion 106 and the retractable portion 107, an angle between the "range" direction of the first ultrasound probe 101 and the non-retractable portion 105 which it is coupled to, and an angle between the "range" direction of the second ultrasound probe 102 and the non-retractable portion 106 which it is coupled to, are comprehensively adjusted, rendering the location relationship of the first ultrasound probe 101 and the second ultrasound probe 102 suitable for assessing e.g. a long bone in the first mode.

Figure 4B:
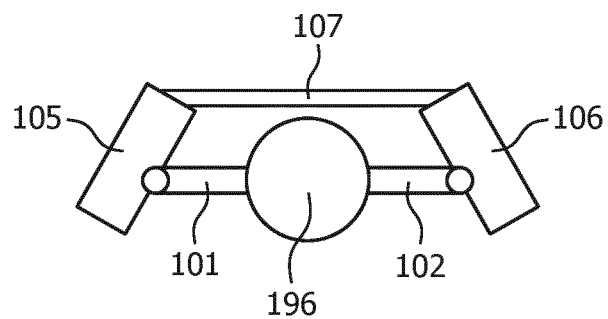
FIG. 4b illustrates a second configuration of the coupler when the coupler comprises a retractable portion which can be retracted into two non-retractable portions according to an embodiment of this invention.

FIG. 4b illustrates a second configuration of the coupler 103 in this embodiment. In the second mode (e.g. the transverse transmission mode), the coupler 103 is in the second configuration, so that the retracted length of the retractable portion 107, the angle between the non-retractable portion 105 and the retractable portion 107, the angle between the non-retractable portion 106 and the retractable portion 107, the angle between the "range" direction of the first ultrasound probe 101 and the non-retractable portion 105 which it is coupled to, and the angle between the "range" direction of the second ultrasound probe 102 and the non-retractable portion 106 which it is coupled to, are comprehensively adjusted, rendering the location relationship of the first ultrasound probe 101 and the second ultrasound probe 102 suitable for assessing e.g. cancellous bones, such as a heel pad, in the second mode.

In the embodiments in FIG. 4a and FIG. 4b, the fourth parameter indicating a distance between the first ultrasound probe 101 and the second ultrasound probe 102 can be determined from the retracted length of the retractable portion 107, the angle between the non-retractable portion 105 and the retractable portion 107, the angle between the non-retractable portion 106 and the retractable portion 107, the angle between the "range" direction of the first ultrasound probe 101 and the non-retractable portion 105 which it is coupled to, and the angle between the "range" direction of the second ultrasound probe 102 and the non-retractable portion 106 which it is coupled to. The "range" direction of an ultrasound probe is to be taken to mean the direction orthogonal to the face of the ultrasound probe as introduced above. The retracted length of the retractable portion 107, the angle between the non-retractable portion 105 and the retractable portion 107, the angle between the non-retractable portion 106 and the retractable portion 107, the angle between the "range" direction of the first ultrasound probe 101 and the non-retractable portion 105 which it is coupled to, and the angle between the "range" direction of the second ultrasound probe 102 and the non-retractable portion 106 which it is coupled to can be measured and then input to the assessing unit 130 manually. As an alternative, the retracted length of the retractable portion 107 can be sensed by a length sensor provided on the retractable portion 107, and the angle between the non-retractable portion 105 and the retractable portion 107, the angle between the non-retractable portion 106 and the retractable portion 107, the angle between the "range" direction of the first ultrasound probe 101 and the non-retractable portion 105 which it is coupled to, and the angle between the "range" direction of the second ultrasound probe 102 and the non-retractable portion 106 which it is coupled to can be obtained by measuring the orientation of the probes, the retractable portion and the non-retractable portions by means of gravity sensors e.g. on the non-retractable portions 105, 106, the retractable portion 107 and the first ultrasound probe 101 and the second ultrasound probe 102, and then input to the assessing unit 130 automatically. Then, the assessing unit 130 can derive the fourth parameter based on these parameters.

In another embodiment, the fourth parameter indicating a distance between the first ultrasound probe 101 and the second ultrasound probe 102 can be measured by a laser measurement method. For example, a laser emitter is located within the first ultrasound probe 101 and a laser receiver is located within the second ultrasound probe 102. Based on the laser speed and the propagation time from the laser emitter to the laser receiver, the fourth parameter indicating a distance between the first ultrasound probe 101 and the second ultrasound probe 102 can be calculated.

As for the third mode (the pulse-echo mode), the coupler 103 may be in the first configuration or second configuration.

In an embodiment, the ultrasound signal comprises a first ultrasound sub-signal in a first frequency band and/or a second ultrasound sub-signal in a second frequency band. The second frequency band is higher than the first frequency band.

For example, the first frequency band is in a low frequency range, e.g. [0.5 MHz, 2 MHz]. The second frequency band is in a high frequency range, e.g. [4 MHz, 6 MHz].

A high-frequency ultrasound signal is suitable for assessing a soft tissue while a low-frequency ultrasound signal is suitable for assessing a bone.

Figure 5A:
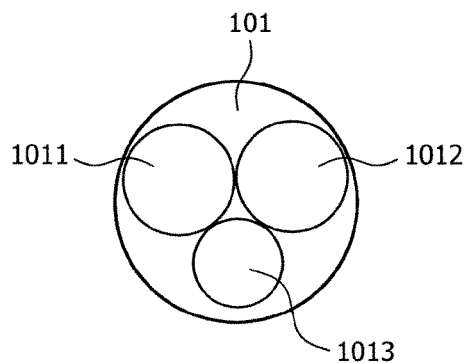
FIG. 5a illustrates a face of the first ultrasound probe which contacts skin of the subject, wherein the first ultrasound probe comprises two ultrasound transducers and a pressure sensor according to an embodiment of this invention.

In an embodiment, as shown in FIG. 5a, the first ultrasound probe 101 comprises two ultrasound transducers 1011, 1012 respectively configured to transmit the first and second ultrasound sub-signal, i.e. the low-frequency sub-signal suitable for bone assessment and the high-frequency sub-signal suitable for soft tissue assessment. For example, each of the two ultrasound transducers 1011, 1022 can be a single-element transducer, or a transducer array.

As a receiving part, the second ultrasound probe 102 may also have two ultrasound transducers (not shown) respectively configured to receive the first and second ultrasound sub-signal, or it may have only one ultrasound transducer (not shown) configured to receive the first and second ultrasound sub-signal (because the first and second ultrasound sub-signal are in different frequency bands, it is easy to separate them).

Figure 5B:
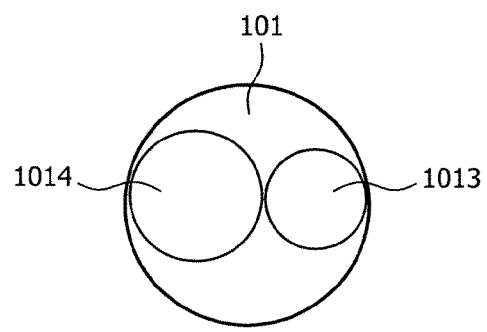
FIG. 5b illustrates a face of the first ultrasound probe which contacts skin of the subject, wherein the first ultrasound probe comprises an ultrasound transducer and a pressure sensor according to an embodiment of this invention.

In an embodiment, as shown in FIG. 5b, the first ultrasound probe 101 comprises a broadband ultrasound transducer 1014 configured to transmit the first and second ultrasound sub-signal, i.e. the low-frequency sub-signal suitable for bone assessment and the high-frequency sub-signal suitable for soft tissue assessment. For example, the broadband ultrasound transducer can be a capacitive micromachined ultrasound transducer (cMUT). For example, the ultrasound transducer 1014 can also be a single-element transducer, or a transducer array.

As a receiving part, the second ultrasound probe 102 may also have a broadband ultrasound transducer (not shown) configured to receive the first and second ultrasound sub-signal (because the first and second ultrasound sub-signal are in different frequency bands, it is easy to separate them), or it may have two ultrasound transducers (not shown) respectively configured to receive the first and second ultrasound sub-signal.

In an embodiment, the assessing unit 130 is configured to derive a third parameter based on the second ultrasound sub-signal, the third parameter indicating a coupling effect caused by soft tissue around the bone. In addition, the assessing unit 130 is further configured to derive the first parameter based on the first ultrasound sub-signal and the derived third parameter, the first parameter indicating one or more characteristics of the bone.

In this way, the coupling effect of the layer of soft tissue overlying the bone on the bone assessment result is at least partially compensated.

In an embodiment, at least one ultrasound probe of the first ultrasound probe 101 and the second ultrasound probe 102 further comprises a pressure sensor 1013 for measuring the pressure applied to the face of the at least one ultrasound probe. The assessing unit 130 is configured to derive the first parameter based on the received ultrasound signal and the measured pressure.

As shown in FIG. 5a and FIG. 5b, a pressure sensor 1013 is present in the first ultrasound probe 101. However, if the second ultrasound probe 102 comprises the pressure sensor 1013, the accuracy of the assessment result is improved as well. If the first ultrasound probe 101 and the second ultrasound probe 102 both comprise the pressure sensor 1013, the accuracy of the assessment result is further improved.

Figure 5C:
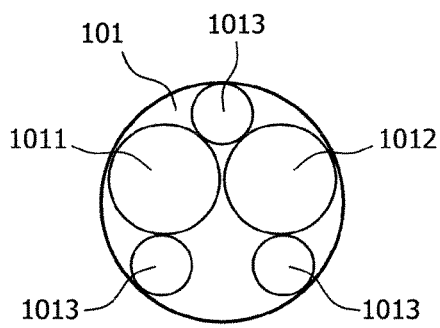
FIG. 5c illustrates a face of the first ultrasound probe which contacts skin of the subject, wherein the first ultrasound probe comprises two ultrasound transducers and three pressure sensors according to an embodiment of this invention.
Figure 5D:
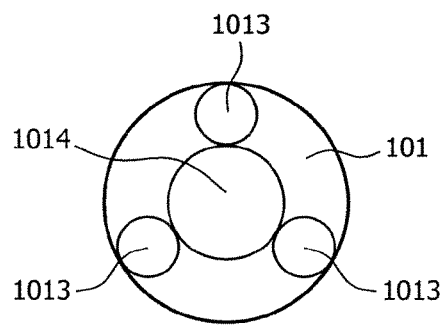
FIG. 5d illustrates a face of the first ultrasound probe which contacts skin of the subject, wherein the first ultrasound probe comprises an ultrasound transducer and three pressure sensors according to an embodiment of this invention.

As shown in FIG. 5c and FIG. 5d, three pressure sensors 1013 are present in the first ultrasound probe 101. The distance between any two of the three pressure sensors is constant. The second ultrasound probe 102 can also comprise three pressure sensors 1013.

It will be appreciated that the number of pressure sensors can be two, four, or any other number which can function in a similar way.

There are many ways to derive the first parameter, based on the received ultrasound signal and the measured pressure. For example, only when the measured pressure is within a predetermined range, the first parameter is derived based on the received ultrasound signal. For another example, a correction factor is computed based on a difference between the measured pressure and a pre-stored standard pressure, and then the first parameter is derived based on the received ultrasound signal and taking the correction factor into consideration.

In an embodiment, each of the two ultrasound transducers 1011, 1012 (in FIG. 5a) or the single ultrasound transducer 1014 (in FIG. 5b) is movable in a certain range so as to measure at a plurality of sites on the subject, the assessing unit 130 is configured to derive the first parameter at each of the plurality of sites, and the ultrasound device 1 further comprises an averaging unit 197 (in FIG. 2) configured to average the first parameters derived at the plurality of sites to obtain an averaged first parameter.

The averaging unit 197 can be realized in many ways. For example, it can be realized by software. Or it can be a logic hardware unit e.g. including a digital adder for adding together the first parameters derived at the plurality of sites, and a digital divider for dividing the added result by the number of sites.

The assessing unit 130 can be realized in many ways. For example, it can be realized by software. For another example, it can be a digital logical circuit which could perform the function of the assessing unit 130.

Figure 6:
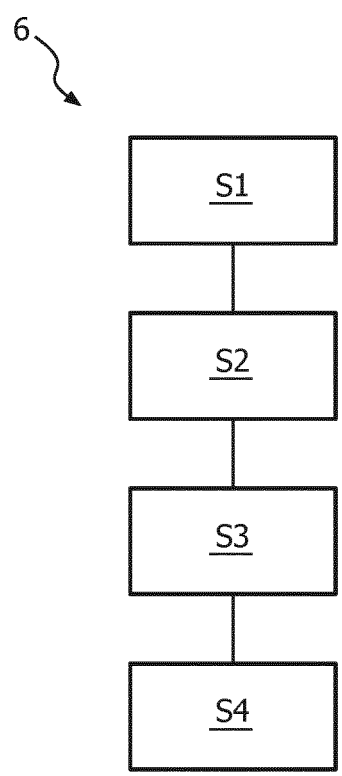
FIG. 6 illustrates a flowchart of the method of assessing a bone of a subject according to an embodiment of this invention.

According to another embodiment of this invention, as shown in FIG. 6, a method 6 is proposed for assessing a bone of a subject in at least two modes comprising a first mode and a second mode using the ultrasound device 1 comprising: at step S1, selecting a mode from the at least two modes; at step S2, transmitting an ultrasound signal to the bone using a first ultrasound probe 101; at step S3, receiving the ultrasound signal from the bone using a second ultrasound probe 102; and at step S4, deriving a first parameter indicating one or more characteristics of the bone based on the selected mode and the ultrasound signal received by the second ultrasound probe 102 in the first or second mode.

Please note that the steps of the methods or units of the devices shown in the present invention should not be limited to the steps or units mentioned above. It will be apparent to those skilled in the art that the various aspects of the invention claimed may be practiced in other embodiments that depart from these specific details.

Furthermore, as can be easily understood by those skilled in the art, several steps in the method claims can be embodied as one step, and one step in the method claims incorporating several actions can be separated into several steps. Also, several units in the apparatus claims can be embodied as one unit, and one unit in the apparatus claims performing several actions can be separated into several units. Such combining and separating falls within the scope of this invention. And, the mere fact that certain measures are recited in mutually different dependent claims does not indicate that a combination of these measures cannot be used to advantage.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The use of the words first, second and third, et cetera, does not indicate any ordering. These words are to be interpreted as names.

The invention claimed is:

1. An ultrasound system for assessing one or more bones of a subject, comprising:
   a first ultrasound probe configured to transmit an ultrasound signal to the one or more bones of the subject;
   a second ultrasound probe configured to receive the ultrasound signal from the one or more bones of the subject;
   a coupler attached to the first ultrasound probe and the second ultrasound probe, the coupler configured to arrange the first and second ultrasound probes in a first configuration associated with a first mode and a second configuration associated with a second mode, wherein the coupler comprises a sensor configured to determine that the coupler is in the first configuration or the second configuration; and
   a digital logic circuit in communication with the first ultrasound probe, the second ultrasound probe, and the sensor, wherein the digital logic circuit is configured to:
      receive, from the sensor, a determination that the coupler is in the first configuration or the second configuration;

derive, when the sensor determines that the coupler is in the first configuration, a first characteristic of the one or more bones using the first mode, the first characteristic derived based on the received determination and the received ultrasound signal; and derive, when the sensor determines that the coupler is in the second configuration, a second characteristic of the one or more bones using the second mode, the second characteristic derived based on the received determination and the received ultrasound signal.

2. The ultrasound system of claim 1, wherein the first ultrasound probe comprises a first face and the second ultrasound probe comprises a second face, and wherein the first face and the second face are oriented in a same direction in the first configuration, and in an opposite direction in the second configuration.

3. The ultrasound system of claim 1, wherein:
the first ultrasound probe is configured to receive an echo signal of the ultrasound signal from the bone in a third mode; and
the digital logic circuit is configured to derive a third characteristic of the bone using a third mode, the third characteristic derived based on the echo signal received by the first ultrasound probe in the third mode.

4. The ultrasound system according to claim 1, wherein the coupler comprises two arms, an intersection angle of the two arms are adjustable, and the first ultrasound probe and the second ultrasound probe are respectively rotatably coupled to ends of the two arms remote from an axis.

5. The ultrasound system of claim 1, wherein the coupler comprises two non-retractable portions and a retractable portion arranged therebetween, which is retractable to different lengths, as required, into the two non-retractable portions, an angle between any of the two non-retractable portions and the retractable portion is adjustable, and the first ultrasound probe and the second ultrasound probe are respectively rotatably coupled to the two non-retractable portions.

6. The ultrasound system of claim 1, wherein the ultrasound signal comprises at least one of a first ultrasound sub-signal in a first frequency band or a second ultrasound sub-signal in a second frequency band, and wherein the second frequency band is higher than the first frequency band.

7. The ultrasound system of claim 1, wherein the first ultrasound probe comprises an ultrasound transducer configured to transmit the first and second ultrasound sub-signals.

8. The ultrasound system of claim 7, wherein the first ultrasound probe is movable in a certain range so as to measure at a plurality of sites on the subject, the digital logic circuit is configured to:
derive the first characteristic at each of the plurality of sites; and average the first characteristic derived at the plurality of sites to obtain an averaged first characteristic.

9. The ultrasound system of claim 7, wherein the first ultrasound probe comprises two ultrasound transducers respectively configured to transmit the first and second ultrasound sub-signals.

10. The ultrasound system of claim 7, wherein each of the two ultrasound transducers is movable in a certain range so as to measure at a plurality of sites on the subject, and wherein the digital logic circuit is configured to:

derive the first characteristic at each of the plurality of sites; and average the first characteristics derived at the plurality of sites to obtain an averaged first characteristic.

11. The ultrasound system of claim 10, wherein the first frequency band is [0.5MHz, 2MHz], and the second frequency band is [4MHz, 6MHz].

12. The ultrasound system of claim 7, wherein the digital logic circuit is configured to:
derive a third characteristic based on the second ultrasound sub-signal, the third characteristic representing a coupling effect caused by soft tissue around the bone; and
derive the first characteristic based on the first ultrasound sub-signal and the derived third characteristic.

13. The ultrasound system of claim 12, wherein
at least one ultrasound probe of the first ultrasound probe and the second ultrasound probe further comprises at least one pressure sensor for measuring the pressure applied to a face of the at least one ultrasound probe; and
the digital logic circuit is configured to derive the first characteristic based on the received ultrasound signal and the measured pressure.

14. The ultrasound system of claim 1, wherein the at least one pressure sensor comprises three pressure sensors, a distance between any two of the three pressure sensors being constant.

15. The ultrasound system of claim 14, wherein the digital logic circuit is configured to derive the first characteristic based on the received determination, the ultrasound signal received by the second ultrasound probe, and a received indication of a distance between the first ultrasound probe and the second ultrasound probe.

16. A method for assessing one or more bones of a subject, the method comprising
transmitting, via a first transducer array, ultrasound signals to one or more bones of a subject;
receiving, via a second transducer array, ultrasound signals from one or more bones of a subject;
arranging, via a coupler, the first and second transducer arrays in a first configuration associated with a first mode and a second configuration associated with a second mode, the coupler comprising a sensor;
determining, via the sensor, whether the coupler is in the first or second configuration;
deriving, via a digital logic circuit and when the coupler is in the first configuration, a first characteristic of the one or more bones using the first mode, the first characteristic derived based on the received determination and received ultrasound signal; and
deriving, via the digital logic circuit and when the coupler is in the second configuration, a second characteristic of the one or more bones using the second mode, the second characteristic based on the received determination and the received ultrasound signal.

17. The method of claim 16, wherein the first transducer array and the second transducer array are oriented in a same direction in the first configuration, and in an opposite direction in the second configuration.

18. The method of claim 16, wherein:
the first transducer array is configured to receive an echo signal of the ultrasound signal from the bone in a third mode; and
the digital logic circuit is configured to derive a third characteristic of the bone using a third mode, the third characteristic derived based on the echo signal received by the first transducer array in the third mode.

19. The method of claim 1, wherein the coupler comprises two arms, an intersection angle of the two arms are adjustable, and the first transducer array and the second transducer array are respectively rotatably coupled to ends of the two arms remote from an axis.

20. The method of claim 16, wherein the coupler comprises two non-retractable portions and a retractable portion arranged therebetween, which is retractable to different lengths, as required, into the two non-retractable portions, an angle between any of the two non-retractable portions and the retractable portion is adjustable, and the first transducer array and the second transducer array are respectively rotatably coupled to the two non-retractable portions.

21. The method of claim 16, wherein the ultrasound signal comprises at least one of a first ultrasound sub-signal in a first frequency band or a second ultrasound sub-signal in a second frequency band, and wherein the second frequency band is higher than the first frequency band.

* * * * *